United States Patent
Kohn

(10) Patent No.: US 9,519,017 B2
(45) Date of Patent: Dec. 13, 2016

(54) CIRCUIT INTEGRITY DETECTION SYSTEM FOR DETECTING THE INTEGRITY OF A SENSING WIRE IN ELECTRICALLY HEATED TEXTILES

(71) Applicant: Sunbeam Products, Inc., Boca Raton, FL (US)

(72) Inventor: Gabriel Kohn, Boca Raton, FL (US)

(73) Assignee: Sunbeam Products, Inc., Boca Raton, FL (US)

( * ) Notice: Subject to any disclaimer, the term of this patent is extended or adjusted under 35 U.S.C. 154(b) by 212 days.

(21) Appl. No.: 14/028,689

(22) Filed: Sep. 17, 2013

(65) Prior Publication Data

US 2015/0008934 A1    Jan. 8, 2015

Related U.S. Application Data

(63) Continuation-in-part of application No. 13/978,645, filed as application No. PCT/US2012/053144 on Aug. 20, 2012, now abandoned.

(60) Provisional application No. 61/551,512, filed on Oct. 26, 2011, provisional application No. 61/640,341, filed on Apr. 30, 2012.

(51) Int. Cl.

| | |
|---|---|
| *G01R 31/14* | (2006.01) |
| *G01R 31/02* | (2006.01) |
| *H05B 3/34* | (2006.01) |
| *H05B 1/02* | (2006.01) |
| *G01N 1/00* | (2006.01) |

(52) U.S. Cl.
CPC ........... *G01R 31/026* (2013.01); *H05B 1/0272* (2013.01); *H05B 3/342* (2013.01); *G01N 1/00* (2013.01); *G01N 2201/00* (2013.01); *H01L 2221/00* (2013.01); *H05B 2203/019* (2013.01); *H05B 2203/02* (2013.01)

(58) Field of Classification Search
CPC .. G01N 1/00; G01N 2201/00; G01N 2203/00; H01L 21/00; H01L 2221/00
See application file for complete search history.

(56) References Cited

U.S. PATENT DOCUMENTS

| | | | |
|---|---|---|---|
| 4,616,124 A * | 10/1986 | Greenhalgh | ................. 219/505 |
| 4,677,281 A * | 6/1987 | Mills | ..................... H02H 5/043 |
| | | | 219/212 |
| 5,422,461 A | 6/1995 | Weiss et al. | |
| 5,422,462 A * | 6/1995 | Kishimoto | .................. 219/545 |
| 6,310,332 B1 | 10/2001 | Gerrard | |
| 6,958,463 B1 | 10/2005 | Kochmann et al. | |
| 7,180,037 B2 | 2/2007 | Weiss | |
| 8,383,992 B2 | 2/2013 | Wang et al. | |
| 2003/0052120 A1 | 3/2003 | Zabrowsky et al. | |
| 2005/0247700 A1 | 11/2005 | Kochman et al. | |
| 2007/0221645 A1 | 9/2007 | Castracane et al. | |
| 2010/0045229 A1* | 2/2010 | Chao | ............................. 318/767 |
| 2010/0051606 A1* | 3/2010 | Lee | ..................... H05B 1/0272 |
| | | | 219/505 |
| 2010/0193503 A1* | 8/2010 | Kim | ....................... H05B 3/56 |
| | | | 219/494 |

(Continued)

*Primary Examiner* — Jermele M Hollington
*Assistant Examiner* — Temilade Rhodes-Vivour
(74) *Attorney, Agent, or Firm* — Seth M. Blum

(57) ABSTRACT

A circuit integrity detection system for use in detecting the integrity of sensing wire in a heating pad wherein the integrity of the sensing wire is checking the inputs from a first and second A/D converter connected to opposite ends of the sensing wire.

5 Claims, 8 Drawing Sheets

(56) References Cited

U.S. PATENT DOCUMENTS

2011/0259872 A1    10/2011  Wang et al.
2012/0199574 A1*   8/2012   Weiss .................... H05B 3/146
                                                        219/481
2013/0264329 A1*   10/2013  Wang ................... H05B 1/0272
                                                        219/477

* cited by examiner

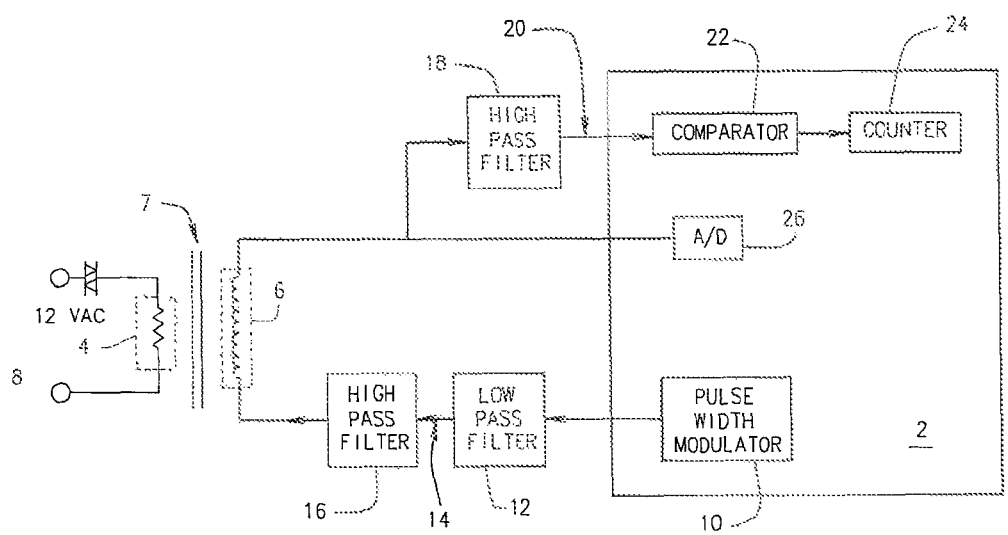
F I G. 4

CIRCUIT INTEGRITY DETECTION SYSTEM FOR DETECTING THE INTEGRITY OF A SENSING WIRE IN ELECTRICALLY HEATED TEXTILES

CROSS-REFERENCE TO RELATED APPLICATION

The present invention is a Continuation-in-part of U.S. application Ser. No. 13/978,645 entitled, A Circuit Integrity Detection System For Detecting The Integrity of a Sensing Wire in Electrical Heated Textiles, filed on Jul. 8, 2013, with is a National Stage Filing of International Application No. PCT/US2012/053144, entitled A Circuit Integrity Detection System For Detecting The Integrity of a Sensing Wire in Electrical Heated Textiles, filed on Aug. 20, 2012, which claims priority to U.S. Provisional Application No. 61/640,341 entitled Enhanced System protection for Heating Pads that Utilize NTC/PTC Sensing Wires, filed on Apr. 30, 2012 and U.S. Provisional Application No. 61/551,512 entitled Enhanced System protection for Heating Pad that Utilize NTC/PTC Sensing Wires, filed on Oct. 26, 2011, the contents of which are herein incorporated by reference in its entirety.

FIELD OF THE INVENTION

The present invention relates to electrically heated textiles hot spot detector and, more particularly, to a system and apparatus for detecting a break in a wire designed to detect hot spots in an electrically heated textile such as a heating pad, electric blanket, electric throw or electric mattress pad.

BACKGROUND OF THE INVENTION

In general, an electrically heated textile is a structure having an electric heating element. The heating element may, for example, be heated by resistance via electricity, and may be provided as one or more metallic wires threaded throughout the pad. The shape and size of the metallic wires may vary, and in some cases the wires may actually be small metallic threads. The heating element typically includes a center heating element constructed of metallic wires having Positive Temperature Coefficient (PTC) characteristics. Around the center PTC wire is a layer of Negative Temperature Coefficient (NTC) material. An electric heating pad is typically plugged into a power outlet so that power may be supplied to the heating element, causing the production of heat. In this manner, the electrically heated textile may be used to warm a desired area of the body. Contemporary heating pads usually include a controller and/or microprocessor which control the amount of heat output from the heating pad.

Some electrically heated textiles also include circuitry designed to detect hot spots. A hot spot occurs when the temperature of any portion of an electrically heated textile exceeds limits designed to prevent a thermal injury to an unsuspecting user. A sensing wire is of low resistance and is typically wound around the NTC layer and it is used provide a path for leakage current and monitor increases in leakage current in the NTC layer caused by heating. However, a break in the sensing wire may result in the inability of the controller to detect hot spots.

One known way to help detect a sensing wire break is to check the voltage of the sensing wire as power is initially applied to the product. When power is first applied, the wire is cold, relatively speaking. As the heating pad gets warmer, the NTC resistance will decrease. This change in resistance can be used to determine if the sensing wire is broken at or in close proximity to the end of the wire, at the point where it is attached to the controller connector. While this may validate the integrity of the sensing wire when the unit is first powered up, it does not work as a continuous "broken sensing wire" detector once the heating pad reaches operating temperatures. Nor, is it capable of detecting a break in the sensing wire that is not close to the end of the NTC/PTC wire where it connects to the controller connector.

Another sensing wire method involves connecting together the two ends of the sensing wire. In this case, compensation is made for a single brake anywhere along the NTC/PTC wire, and continuous detection of hot spots is not affected. However, it is not possible to know that a break in the sensing wire has occurred. Additionally, if a second wire break occurs, loss of hot spot detection is very possible. Specifically hot spot detection is lost between the two wire breaks.

It is therefore desirable to provide a detection system that will continuously check the integrity of the sensing wire. If the sensing wire breaks at any time during use and for any reason, the system will shut down and prevent the use of the product.

SUMMARY OF THE INVENTION

The present invention includes a system and apparatus for monitoring the condition of an electrically heating textile sensing wire to determine whether a break in the sensing wire has occurred. In one embodiment, the condition of the sensing wire can be determined without disengaging the heating circuitry within the electrically heating textile. The heating circuitry may operate at a generally standard 50-60 Hz AC line voltage, such that the sensing wire may normally operate at a corresponding frequency. In addition to this signal, integrity of the sensing wire may be determined by first driving one end of the sensing wire with a low voltage electrical test signal from a microcontroller, and then checking whether the test signal is present on the other end of the sensing wire. In order to distinguish the test signal from the standard AC line voltage present on the sensing wire, the electrical test signal is preferably of a different frequency than the standard 50-60 Hz AC line voltage. In one embodiment, the test signal frequency is approximately 30 kHz. Other frequencies and voltages for the test signal may also be used.

In one embodiment, a sensing wire is positioned to detect and/or measure heating of an electrically heating textile. Preferably, the sensing wire is wrapped around a negative temperature coefficient (NTC) material, and each end of the sensing wire is connected to a microcontroller. At one end of the sensing wire, a pulse width modulator within the microcontroller creates a low voltage electrical test signal. So that the test signal may be distinguished from the 50-60 Hz AC line voltage at which temperature monitoring on the sensing wire occurs, the test signal is preferably at a very different frequency, and more preferably at about 30 GHz. This test signal is passed through low-pass filter to reduce undesirable higher frequency signal components, and becomes the signal "DRIVE." The DRIVE signal is then passed through a high pass filter to isolate the DRIVE test signal generation circuit from the AC line voltage.

The test signal then passes through the wound sensing wire. Before connecting back to the microcontroller, the sensing wire and signals preferably split. One prong continues to the microcontroller's analogue/digital converter for standard sensing purposes, while the other prong preferably passes through a high-pass filter to filter out the lower frequency AC line voltage, resulting in a "RETURN" signal. The RETURN signal may then enter the microcontroller. If the sensing wire is unbroken, the RETURN signal will generally vary in magnitude, but will be at the same frequency as the DRIVE signal.

Within the microcontroller, the RETURN signal is sent to a comparator which will output a transition at each transition of the RETURN test signal. A counter counts the number of transitions over a period of time. If the microcontroller detects at least a predetermined threshold number of transitions of the comparator, the sensing wire is determined to be intact. However, where fewer than the threshold number of transitions is counted, the sensing wire is determined to be broken. The microcontroller then preferably disables the heating elements of the heating pad for safety purposes.

As will be understood, other frequencies may be used for the DRIVE test signal. However, changes in DRIVE test signal frequencies may necessitate different filters, such as a specific band-pass filter, to ensure that the DRIVE test signal frequency is properly applied to and extracted from the sensing wire. Additionally, some or all of the filters, comparator, counter, modulator and A/D converter may be present on the microcontroller or may be separate from the microcontroller.

DESCRIPTION OF THE DRAWINGS

FIG. 4 is a block diagram of a microcontroller and sensing wire configuration according to the teachings of the present invention.

It should be understood that the present drawings are not necessarily to scale and that the embodiments disclosed herein are sometimes illustrated by fragmentary views. In certain instances, details which are not necessary for an understanding of the present invention or which render other details difficult to perceive may have been omitted. It should also be understood that the invention is not necessarily limited to the particular embodiments illustrated herein. Like numbers utilized, throughout the various figures designate like or similar parts or structure.

DETAILED DESCRIPTION

Figure 1:
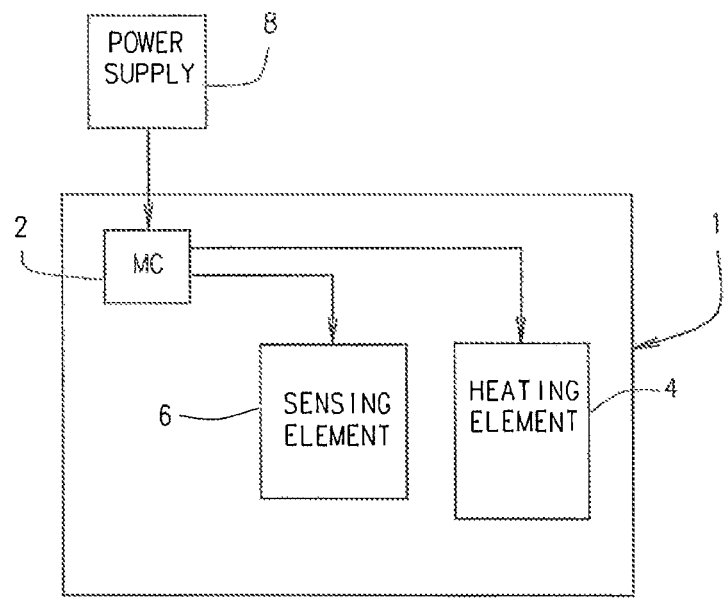
FIG. 1 is a block diagram of a prior art heating pad.

Referring now to the drawings and, more particularly, to FIG. 1, a block diagram of a prior art electrically heating textile, such as a heating pad 1 is shown. Heating pad 1 includes a heating pad controller 2, which may include a microprocessor or microcontroller, for controlling the operation of the heating pad 1. Microcontroller 2 is in electrical communication with a heating element 4, and supplies power to the heating element 4 to heat the heating pad 1. Alternatively, microcontroller 2 may be located outside of the heating pad. Microcontroller 2 is also in electrical communication with sensing element 6. Sensing element 6 is a safety feature designed to detect hot spots in heating pad 1. Upon detection of a hot spot, microcontroller 2 generally deactivates or reduces power to heating element 4 until the hot spot is no longer present. A power supply 8 is generally electrically connected to microcontroller 2 to provide electrical power thereto. Power supply 8 is generally incorporated into the microcontroller 2, but may be a plug connected to a standard wall outlet, or batteries, or another source of electrical power.

Figure 2:
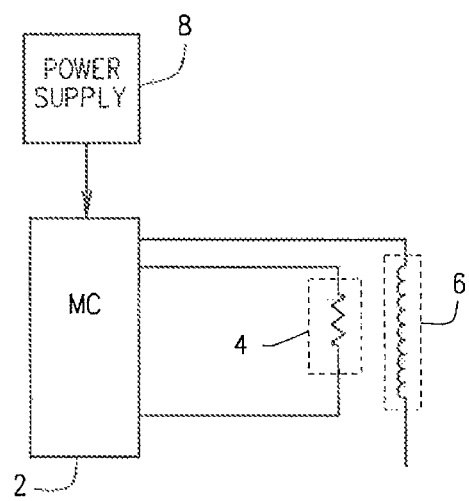
FIG. 2 is a schematic block diagram of a prior art sensing wire configuration.

FIG. 2 is a schematic block diagram of a prior art sensing wire configuration. Microcontroller 2 is connected to a heating element 4 comprised of a resistor which generates heat as current passes therethrough. Generally, the resistor of heating element 4 is comprised of a material with Positive Temperature Coefficient (PTC) characteristics. A material (not shown in FIG. 2) having Negative Temperature Coefficient (NTC) characteristics is then wrapped around the heating element 4, and a sensing element 6 (shown as a sensing wire in FIG. 2) of relatively low resistance is wrapped around the NTC material. The sensing element 6 is generally connected at one end to the microcontroller 2, and the other end is left open.

In operation, power is supplied by the microcontroller 2 to the heating element 4, which causes the heating element 4 to emit heat. The resistance of heating element 4 increases as its temperature increases due to its PTC characteristics. In one prior art embodiment, the microcontroller 2 can attempt to determine the temperature of the heating element 4 based upon its resistance. However, only average heating pad temperature information can be extracted from the PTC heating element. The resistance of the NTC material decreases as the temperature increases. This change in resistance can be detected by the sensing element 6, providing localized temperature information, and the microcontroller 2 can thereby detect hot spots anywhere along the heating element 4. Generally, when a hot spot exceeds a predetermined threshold temperature, the microcontroller 2 deactivates the heating element 4 or reduces power as a safety mechanism. However, a break in the sensing element 6 may result in the inability of the microcontroller 2 to detect such hot spots.

Figure 3A:
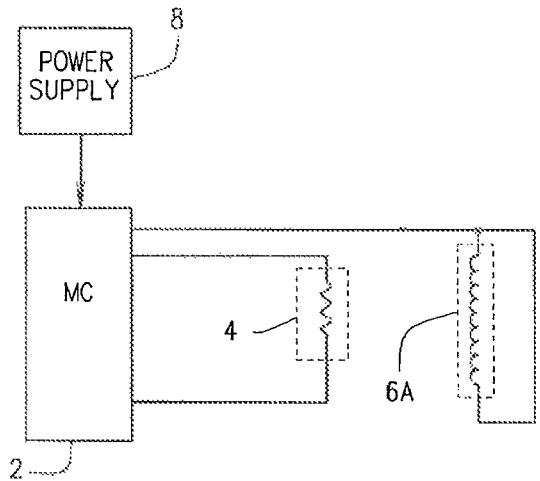
FIG. 3A is a block diagram of another prior art sensing wire configuration, in which the sensing wire is intact.
Figure 3B:
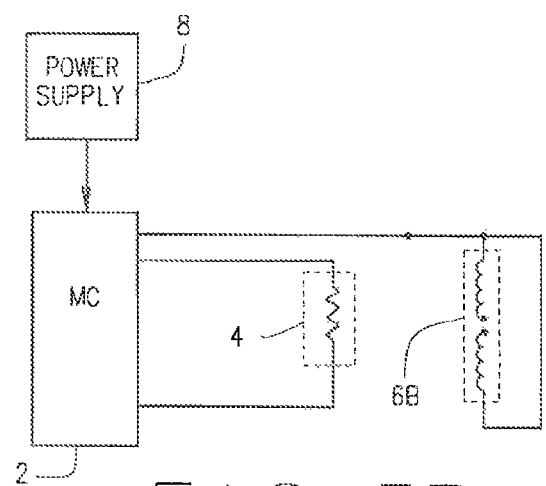
FIG. 3B is a block diagram of the sensing wire configuration of FIG. 3A, in which the sensing wire has one break.
Figure 3C:
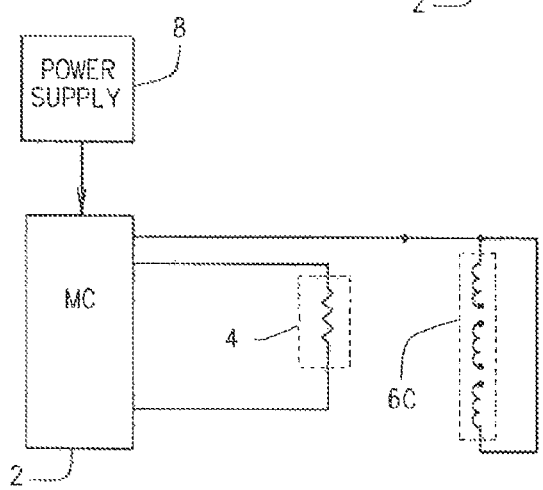
FIG. 3C is a block diagram of the sensing wire configuration of FIG. 3A, in which the sensing wire has two breaks.

FIG. 3A is a schematic block diagram of another prior art sensing wire configuration. In this prior art embodiment, the two ends of sensing element 6 are connected together. Although the sensing element 6 can continue to detect hotspots largely anywhere along the sensing element 6 even where a single break in the sensing element 6 occurs (as is illustrated in FIG. 3B), the break itself is not detectable in this configuration. Further, in FIG. 3C, there are two separate breaks in the sensing element 6. The sensing element 6 is no longer capable of detecting a hot spot between the two breaks in the sensing element 6.

FIG. 4 illustrates a block diagram of a sensing wire integrity detection system according to one embodiment of the present invention. As above, sensing element 6 detects hot spots created by heating element 4 through an NTC material 7. Such monitoring in the sensing element 6 occurs in the presence of an AC line voltage of about 50-60 Hz in one embodiment. It is noted that different frequencies may also occur instead of or in addition to the 50-60 Hz range. Microcontroller 2 may include a test signal generator which is shown in FIG. 4 as a pulse width modulator 10. Such a test signal generator may alternatively be separate from the microcontroller 2. Pulse width modulator 10 preferably generates a signal which has a frequency different from that of the AC line voltage. In an embodiment where the AC line voltage frequency is about 50-60 Hz as described above, pulse width modulator may generate a test signal at a frequency of about 30 kHz.

This test signal is then preferably passed through a low pass filter 12 to reduce undesirable higher frequency signal components, and the signal becomes the DRIVE signal 14. DRIVE signal 14 is then preferably passed through a high pass filter 16 before encountering sensing element 6. High pass filter 16 preferably isolates the pulse width modulator 10 and low pass filter 12 from the AC line voltage. The DRIVE signal 14 then passes to one end of the sensing element 6. Either or both of the low pass filter 12 and the high pass filter 16 may be components of microcontroller 2 or may be separate therefrom.

Any signal passing through the sensing element 6 is preferably passed through a high pass filter 18 to filter out the AC line voltage. As above, the high pass filter 18 may be a component of microcontroller 2, or may be separate therefrom. Any signal which passes the high pass filter 18 is labeled RETURN signal 20. The RETURN signal 20 is then passed to a signal detector component, which includes comparator 22 as shown in FIG. 4. Comparator 22 preferably compares the RETURN signal 20 to a threshold voltage, which may be about one volt. Where the sensing element 6 is intact, the RETURN signal 20 will vary in magnitude, but will be at the same frequency and have generally the same wave shape as the DRIVE signal 14 with, for example, a magnitude of approximately two volts or more. Thus, the comparator 22 output transitions at each transition of the RETURN signal 20. A counter 24 counts the number of transitions of comparator 22. The first, second, or both ends of the sensing element 6 may pass directly to an analogue to digital converter (A/D) 26 for standard hot spot detection purposes. It is noted that, as above, any or all of the high pass filter 18, comparator 22, counter 24 and/or A/D 26 may be components of microcontroller 2 or may be separate therefrom.

Microcontroller 2, which may include firmware, or may execute software, determines whether or not the electrical test signal, RETURN Signal 20, is being returned (indicating whether or not the integrity of the sensing wire is good) by looking for comparator output transitions at the proper frequency. This is accomplished by counting the number of comparator output transitions over a fixed period of time. False counts from spurious sources such as electrical noise and AC line voltage transitions that might appear at the comparator input are eliminated by looking for an expected number of transitions using a minimum value as a threshold.

It is noted that comparator 22 may alternatively be an A/D converter, such that the RETURN signal 20 could be converted to a digital number whose value represents the amplitude of signal 20. The presence of a digital number whose value exceeds a predetermined threshold would indicate that signal 20 is of valid amplitude. A predetermined number of valid amplitude pulses of signal 20 during a period of time would indicate that the sense wire is intact. The predetermined number of pulses is preferably equal to the number of pulses present on the DRIVE signal 14.

Figure 5:
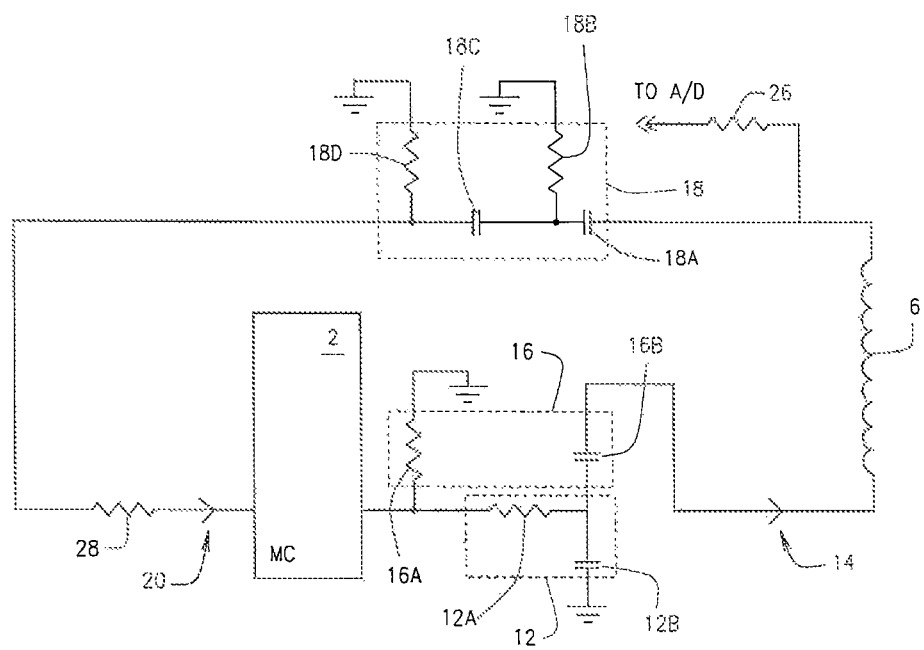
FIG. 5 is an exemplary schematic circuit diagram according to the block diagram of FIG. 4.

FIG. 5 illustrates a schematic circuit diagram of one possible configuration for a sensing wire integrity detection system. Microcontroller 2 may be any suitable chip, but for the purposes of this disclosure, microcontroller 2 will be discussed as a PIC16F1827-I/SO chip. Pin three of microcontroller 2 preferably outputs a 30,000 Hz low voltage signal. This 30 kHz signal then passes through a low pass filter 12 formed by a 1-kΩ resistor 12A and a 2.2 nF capacitor 12B, as well as a high pass filter 16 formed by a 2.2 nF blocking capacitor 10B and a 2.4-kΩ resistor 16A. The DRIVE signal then passes through the sensing element 6, and thereafter the DRIVE signal is isolated from the lower frequency line voltage signal by another high pass filter 18 formed by two 1-nF capacitors 18A and 18C, as well as two 10-kΩ resistors 18B and 18D. The filtered RETURN signal is then input to pin one of microcontroller 2. As will be recognized, other hardware configurations, resistances, capacitances, etc. may alternatively be used.

Figure 6:
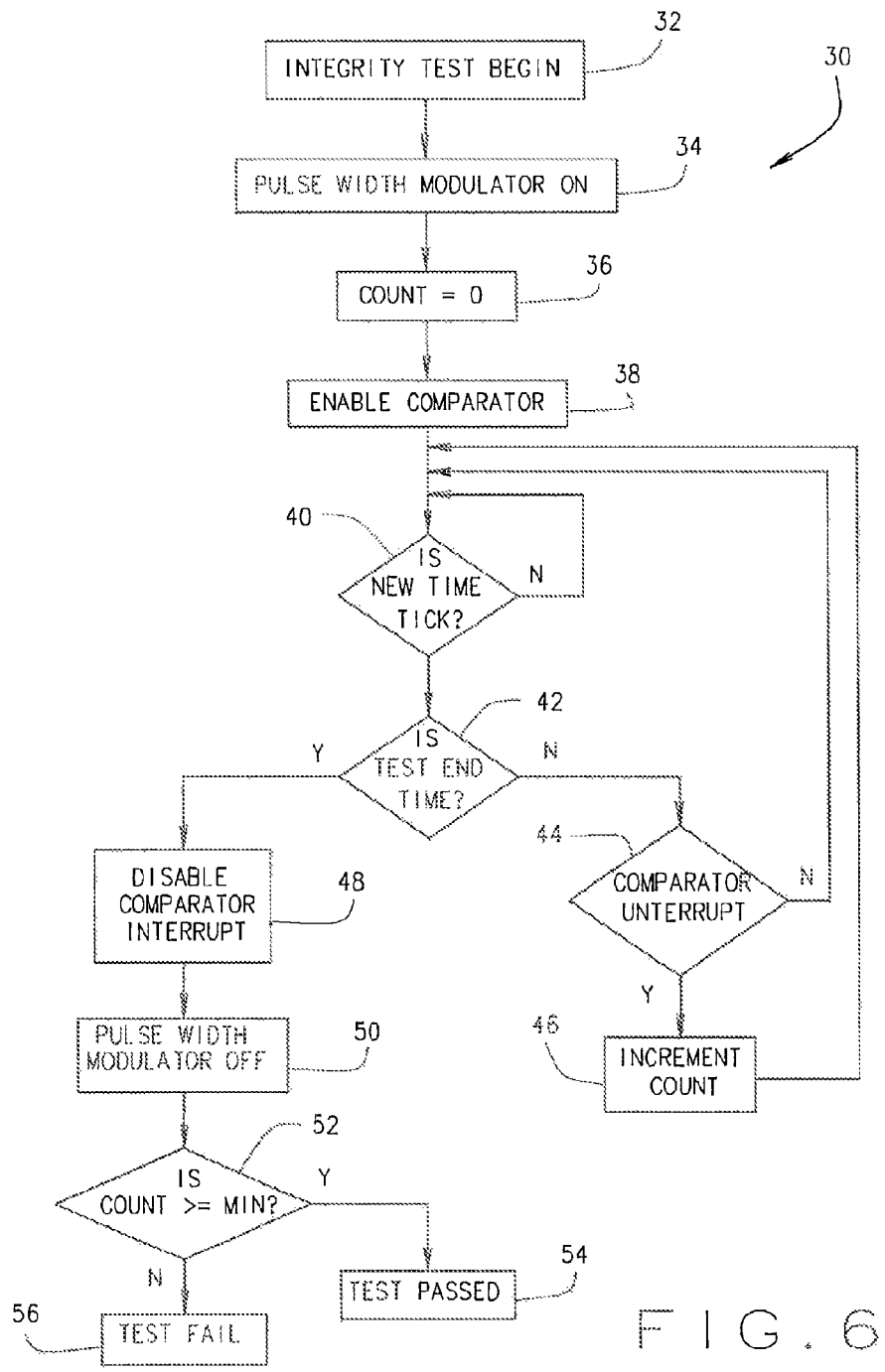
FIG. 6 is a flow chart of a method for determining the integrity of a sensing wire according to the teachings of the present invention.

FIG. 6 illustrates a method 30 for determining the integrity of a sensing element. At step 32, the integrity test begins. At step 34, the DRIVE signal is turned on, such that pulse wave modulator 10 generates a signal at a different frequency from that of the AC line voltage in the sensing element 6. At step 36 the count in counter 24 is set to zero, and at step 38 the comparator 22 interrupt is enabled.

At step 40, microcontroller 2 determines whether a new time-tick has occurred. Where no new time-tick has occurred, the process reverts back to step 40. When a new time-tick occurs, the process moves to step 42 where the microcontroller 2 determines whether the test is at its end time. Where the test is not at its end time, the microcontroller 2 determines whether the comparator 22 has transitioned. As discussed above, the comparator 22 compares the RETURN signal to a threshold voltage which is in one embodiment about one volt, and the comparator output transitions with each transition of the RETURN signal at the proper frequency. Where comparator 22 has transitioned at step 44, counter 24 increments its count by one at step 46. The method then returns to step 40 to await a new time-tick.

At step 42, if the test is at its end time, the method proceeds to step 48 where the comparator 22 interrupt is disabled, along with the DRIVE signal at step 50. At step 52, the microcontroller 2 determines whether the count from counter 24 is greater than or equal to a minimum threshold count. The minimum threshold count is designed to compensate for any spurious sources such as electrical noise and/or AC line voltage transitions that may appear. If the count from counter 24 is greater than or equal to the minimum threshold count, the microcontroller determines that the test has been passed at step 54, and the sensing element 6 is intact. However, where the count from counter 24 is less than the minimum threshold count at step 52, the microcontroller 2 determines that the test has been failed at step 56. With a failed test, microcontroller 2 preferably deactivates the heating element 4 to protect the user.

Pulse width modulator 10 may be selectively engaged to generate DRIVE signal 14 intermittently, or may run continuously. Similarly, microprocessor 2 may selectively check for the RETURN signal 20 at preselected intervals or may constantly monitor for RETURN signal 20 to continuously monitor the integrity of sensing wire 6.

Figure 7:
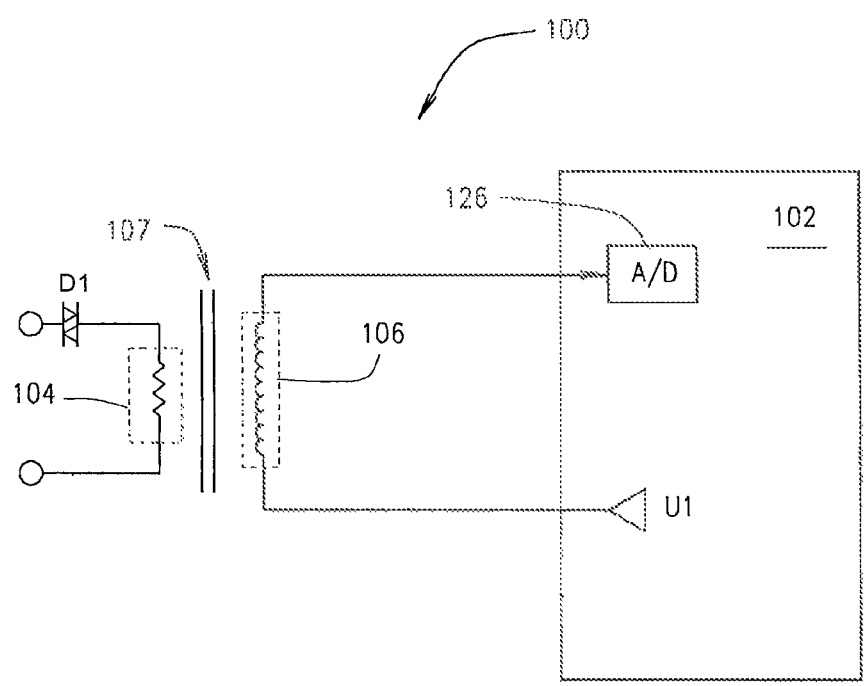
FIG. 7 illustrates an alternative embodiment of a sensing wire integrity detection system according to the teachings of the present invention.

FIG. 7 illustrates an alternate embodiment of a sensing wire integrity detection system 100, winch includes a microcontroller 102, a heating element 104, an NTC layer 107, a sensing element 106, and an A/D converter 126, as in the above discussed embodiments.

In this embodiment, in order to detect the integrity of sensing wire 106, at fixed intervals, power to the heating element 104 is removed and/or disengaged while the test signal is being applied to sensing wire 106. This cut in power to the heating element 104 may be for a duration of for example, one power line cycle of 16.66 milliseconds, or any other fixed time period. Microprocessor output U1 provides a series of square waves during the periods that Triac D1 is forced to become inactive. Appropriate filtering is used to separate the AC line frequency from the signal the U1 provides and separate A/D inputs are used for detecting hot spots and sense wire integrity signals.

Figure 8:
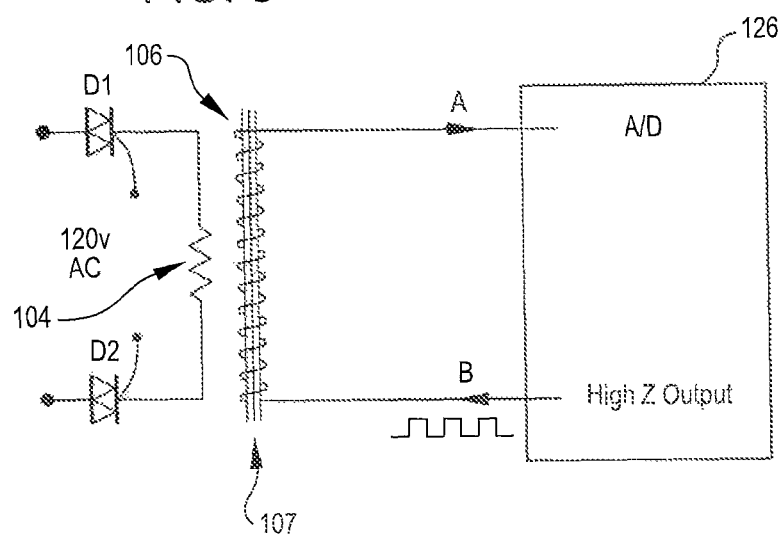
FIG. 8 illustrates an alternative embodiment of a sensing wire integrity detection system according to the teachings of the present invention.

In another embodiment, as show in FIG. 8, the integrity of the sensing wire 106 can be determined by disconnecting the NTC layer 107 from the AC power, at some intervals for a selected period of time. Upon which the sensing wire integrity circuit is engaged, providing a test signal through the sensing wire.

In the heating phase, triacs D1 and D2 are "on" and pin B is in a high Z state. NTC 107 leakage is measured by the A/D 126 to detect hot spots. In a testing phase, triacs D1 and D2 are shut "off" and pin B outputs a signal, for example as square wave, that passes through the sensing wire 106 to the A/D 126. The integrity of the sensing wire is determined by checking the amplitude of the signal received by the A/D 126 and counting the number of square wave pulses that have been received versus how many were sent.

One verification of the sensing wire 106 integrity is complete (i.e., the appropriate amplitude of the signal and/or the number of square wave pulses are detected by A/D 126), the power to the heating element 104 is resumed, triacs D1 and D2 are "on" and pin B is in a high Z state. Such a process may be repeated as needed and the verification test cycle can be again initiated by microcontroller 102.

Figure 9:
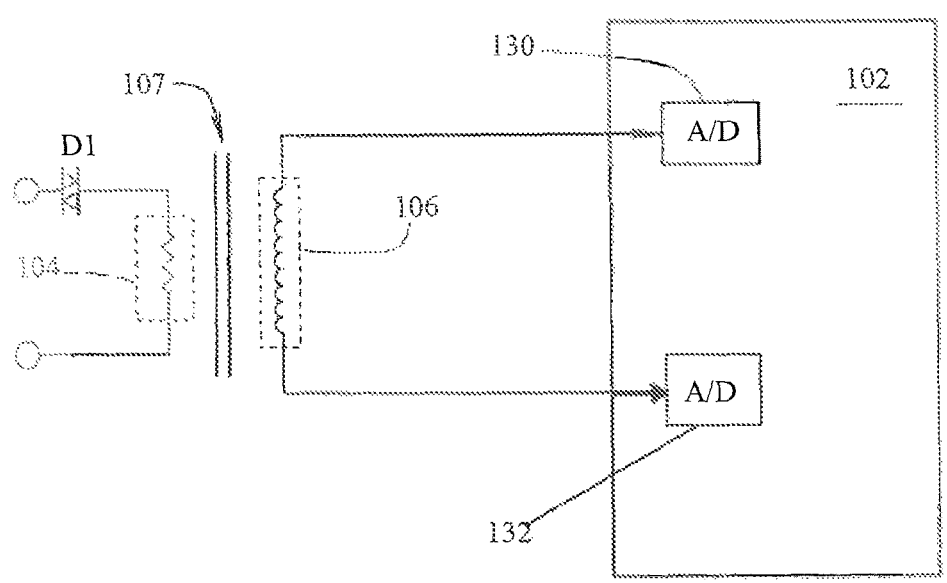
FIG. 9 illustrates an alternative embodiment of a sensing wire integrity detection system according to the teachings of the present invention.

FIG. 9 illustrates an alternate embodiment of a sensing wire integrity detection system 100, which includes a microcontroller 102, a heating element 104, an NTC layer 107, a sensing element 106, and a first A/D converter 130 and a second A/D converter 132.

In this embodiment, the integrity of sensing wire 106 is detected by the microcontroller 102 polling the information provided by the first and second AO converters 130 and 132. The inputs from the first and second A/D converters 130 and 132 can be as follows:

1) No sensing wire 106 breaks—normal operating temperature:
   A/D 130=A/D 132 and A/D 130 input<x volts.
   No action required by controller 102
2) No sensing wire 106 breaks—Hot spot:
   A/D 130=A/D 132 and A/D 130 input>x volts.
   Controller 102 will reduce or remove power to heating element 104
3) Broken Sensing Wire—Normal Operating Temperature:
   A/D 130=A/D 132 and A/D 130 input<x volts.
   No action required by controller 102
4) Broken Sensing Wire—Hot Spot:
   A/D 130≠A/D 132.
   Controller 102 will active safety circuit to disable controller 102.
5) Broken Sensing Wire—Hot Spot located on break
   A/D 130=A/D 132; and A/D 130 and A/D 132 inputs<x volts
   Controller 102 will reduce or remove power to heating element 104

Where x volts is a threshold voltage directly related to the temperature in the NTC layer 107. As the temperature in the NTC layer 107 increases, the resistance of the NTC wire 107 decreases resulting in an increased voltage to the AD converter 130. The threshold temperature in the NTC layer 107 is the temperature at which a "hot spot" in present in the NTC layer 107.

Under condition 4, Broken Sense Wire—Hot Spot, there will be a difference between the inputs from the first and second A/D converters 130 and 132, at which point the microcontroller 102 preferably deactivates the heating element to protect the user. The deactivation of the heating element 104 can include the blowing of a fuse to disabling to the controller 102

Thus, there has been shown and described several embodiments of a novel heating pad safety system and method. As is evident from the foregoing description, certain aspects of the present invention are not limited by the particular details of the examples illustrated herein, and it is therefore contemplated that other modifications and applications, or equivalents thereof, will occur to those skilled in the art. The terms "having" and "including" and similar terms as used in the foregoing specification are used in the sense of "optional" or "may include" and not as "required". Many changes, modifications, variations and other uses and applications of the present invention will, however, become apparent to those skilled in the art after considering the specification and the accompanying drawings. All such changes, modifications, variations and other uses and applications which do not depart from the spirit and scope of the invention are deemed to be covered by the invention which is limited only by the claims which follow.

What is claimed is:

1. An electrically heated textile comprising:
   a heating element, wherein a first signal is generated through the heating element at a first frequency;
   a sensing wire for detecting a hotspot created by the heating element;
   a layer having a negative temperature coefficient (NTC) positioned between the heating element and the sensing wire, wherein the sensing layer is wrapped about the NTC layer; and
   a means for detecting the integrity of a sensing wire including a first A/D converter connected to a first end of the sensing wire; a second A/D converter connected to a second end of the sensing wire; and a signal detector for detecting the signal from the first and second A/D converters.

2. The electrically heated textile as recited in claim 1, wherein when the signal from the first A/D converter equals the signal from the second A/D converter, and the voltage in the first A/D convert is less than x volts, there is no breaks in the sensing wire and no hot spots in the heating element.

3. The electrically heated textile as recited in claim 1, wherein when the signal from the first A/D converter equal the signal from the second A/D converter, and the voltage in the first A/D convert is greater then x volts, there is no breaks in the sensing wire and a hot spot in the heating element.

4. The electrically heated textile as recited in claim 1, wherein when the signal from the first A/D converter equal the signal from the second A/D converter, and the voltage in the first A/D convert is less then x volts, there can be a break in the sensing wire and no hot spots in the heating element.

5. The electrically heated textile as recited in claim 1, wherein when the signal from the first A/D converter does not equal the signal from the second A/D converter there is a break in the sensing wire and a hot spot in heating element.

* * * * *